US012562491B2

(12) United States Patent \
Shah et al.

(10) Patent No.: US 12,562,491 B2 \
(45) Date of Patent: Feb. 24, 2026

(54) ANTENNA ASSEMBLY FOR A TOMOGRAPHY SYSTEM

(71) Applicant: Forschungszentrum Jülich GmbH, Jülich (DE)

(72) Inventors: Nadim Joni Shah, Jülich (DE); Chang-Hoon Choi, Jülich (DE); Jörg Felder, Jülich (DE); Suk-Min Hong, Würselen (DE)

(73) Assignee: Forschungszentrum Jülich GmbH (DE)

( * ) Notice: Subject to any disclaimer, the term of this patent is extended or adjusted under 35 U.S.C. 154(b) by 80 days.

(21) Appl. No.: 18/581,030

(22) Filed: Feb. 19, 2024

(65) Prior Publication Data

US 2024/0291156 A1 Aug. 29, 2024

(30) Foreign Application Priority Data

Feb. 23, 2023 (DE) .......................... 102023201651.6

(51) Int. Cl.
| | |
|---|---|
| *H01Q 9/42* | (2006.01) |
| *G01R 33/34* | (2006.01) |
| *A61B 5/00* | (2006.01) |

(52) U.S. Cl.
CPC .............. *H01Q 9/42* (2013.01); *G01R 33/34* (2013.01); *A61B 5/0055* (2013.01)

(58) Field of Classification Search
CPC ........ H01Q 9/42; G01R 33/34; G01R 33/481; A61B 5/0055; A61B 5/055
See application file for complete search history.

(56) References Cited

U.S. PATENT DOCUMENTS 11,378,675 B2 * 7/2022 Biber ............... G01R 33/56509

FOREIGN PATENT DOCUMENTS

DE 102019003949 A1 12/2020

OTHER PUBLICATIONS

Yong Pang, et al., Tilted Microstep Phased Arrays With Improved Electromagnetic Decoupling for Ultrahigh-Field Magnetic Resonance Imaging, www.md-journal.com, Dec. 2014, 6 pages.
5.4 Elektromagnetische Wellen, Jun. 27, 2001, 14 pages.

* cited by examiner

*Primary Examiner* — Seung H Lee

(74) *Attorney, Agent, or Firm* — Barnes & Thornburg

(57) ABSTRACT

The present disclosure relates to an antenna assembly for an imaging method, a use of an antenna assembly and a tomography system, in particular for MRI or simultaneous MR-PET/SPECT. An antenna assembly for an imaging method comprises at least two adjacent antennas, wherein each of the at least two antennas is designed as a J-pole antenna with a radiation section and a feed section. The at least two antennas are arranged alternately at a first angle and a second angle different from the first angle in relation to a reference surface. In this way, effective decoupling of the two antennas is achieved by simple means.

19 Claims, 3 Drawing Sheets

ANTENNA ASSEMBLY FOR A TOMOGRAPHY SYSTEM

PRIORITY CLAIM

Figure 1:
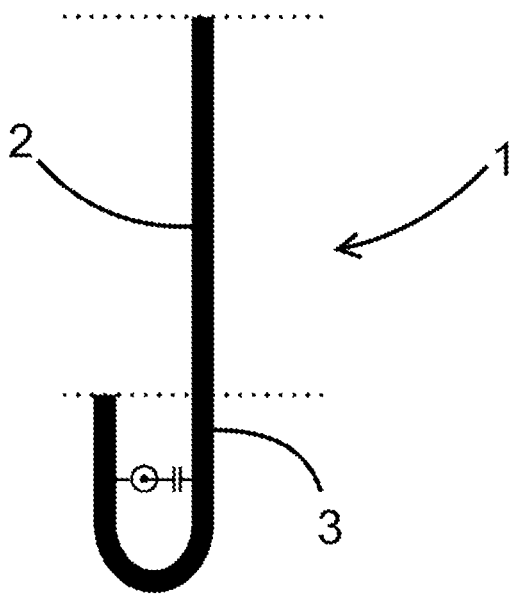

This application claims priority to German Application 102023201651.6, filed Feb. 23, 2023, which application is hereby incorporated in its entirety herein.

FIELD OF THE DISCLOSURE

The present disclosure relates to an antenna assembly for an imaging method, a use of an antenna assembly and a tomography system, in particular for MRI or simultaneous MR-PET/SPECT.

BACKGROUND

Magnetic resonance imaging (MRI) is a non-invasive imaging method for examining parts of the body, with which high-resolution sectional images of the body can be generated for medical diagnostics. It is based on the resonant excitation of certain atomic nuclei included in the body or supplied to the body by means of strong magnetic fields and alternating magnetic fields in the radio frequency range (nuclear magnetic resonance), which cause the induction of an electrical signal in a receiving antenna. In this way, high-resolution images can be generated.

To perform MRI, high-frequency antennas—also known as coils in MRI—are used, which are positioned on or around the body or body part to be examined. The arrangement close to the body is particularly the case with ultra-high field MRI (magnetic flux density≥7T) in order to enable a greater penetration depth and generate a symmetrical B1 field pattern. Antenna assemblies with multiple antennas, also known as multichannel antennas or multichannel (antenna) arrays, are used to generate a more homogeneous or spatially extended magnetic field, increase coverage and/or accelerate image acquisition. An antenna assembly can also be used to optimally cover certain parts of the body. An antenna assembly allows the arrangement of a number and possibly shape and/or size of antennas adapted to the respective case, in other words it can be provided as a personalized/dedicated antenna assembly.

Due to the mutual coupling of the antennas in an antenna assembly, interference occurs between the antennas of an antenna assembly as a result of mutual coupling. This is due to electromagnetic interaction between the individual antennas. This leads to a change in the radiation pattern and the input impedance. Additional modes in the frequency spectrum are the result. In addition, the efficiency of power transmission and the ability to improve homogeneity by BI shimming or with the parallel transmission method are reduced. The coupling of two antennas decreases with increasing distance and angle. This limits the number of antennas per area and/or volume and therefore the achievable resolution (via the achievable SNR) of the imaging method. Substantial effects of coupling are an increased power requirement and a reduction in the coding capacity, which is caused by a reduction in the different field distributions of the individual antennas.

Various methods are known for decoupling, such as partial overlapping, inductive decoupling, capacitive decoupling, magnetic wall decoupling, self-decoupling, induced current compensation or elimination (ICE) or a filter network between the antennas. However, these are usually technically complex, have considerable disadvantages and/ or are not suitable for all relevant imaging methods. A J-pole antenna is described in WO 2020 244 689 A1.

SUMMARY

The present disclosure provides an improved antenna assembly, use and an improved tomography system.

An antenna assembly for an imaging method is described herein. The antenna assembly comprises at least two antennas arranged adjacent to each other. Each of the at least two antennas is configured as a J-pole antenna with a radiation section and a feed section. The at least two adjacent antennas are arranged alternately at a first angle and a second angle different from the first angle with respect to a reference surface.

An effective electromagnetic decoupling of the two antennas from each other is achieved by the arrangement of the antennas in alternately different angles. More precisely, the coupling factor is improved (reduced). This allows the image quality to be improved. In addition, more channels, i.e., more antennas, can be arranged per area and/or volume, which improves the power of parallel transmission and thus also the uniformity or homogeneity of the B1 field and increases the signal-to-noise ratio. This further improves the quality and informative value of the image.

A J-pole antenna is a J-shaped antenna with an essentially straight radiation section and a curved, for example U-shaped feed section. The radiation section is configured in particular for transmitting and/or receiving electromagnetic radiation. In particular, the feed section is configured to feed the radiation section. The radiation section and feed section are electrically connected to each other. In particular, the radiation section merges seamlessly into one leg of the U-shaped feed section.

A J-pole antenna can also be referred to as a dipole antenna element. Such an antenna is described in detail in the publication WO 2020 244 689 A1. A J-pole antenna is designed in particular in such a way that it has a fold at one end, which consists of a bend, a bent area and the projection of the bent area onto the length of the J-pole antenna. One leg is longer than the other leg so that a characteristic J-shape is formed. In particular, the two legs are arranged at least essentially parallel to each other. In particular, the bend is realized as a curve. In some designs, the longer leg is the radiation section and the bent area or the shorter leg is the feed section. The antenna can therefore be an end-fed antenna. In particular, the feed section is configured such that it enables the connection of at least one further component, in particular for feeding the antenna. In particular, the radiation section has no connections.

The length of the radiation section is preferably $\lambda/2$. The length of the radiation section means the length of the longer leg from its outermost point to the point at which the projection of the bent area begins. The length of the feed section is preferably $\lambda/4$. The length of the feed section means the length of the shorter leg from the point at which the projection of the bent area begins to the outermost point of the bend. Typically, the lengths are measured along the same straight line. Preferably, the radiation sections of the antennas run parallel to each other Depending on the desired frequency and target object, the lengths can be adjusted, shortened or extended using various methods.

The angle between an antenna and the reference surface is measured between a plane of the antenna and the reference surface. In each case, the smaller of the two possible angles is meant. Accordingly, each angle is at most 180°. In principle, arbitrary first and second angle can be used. Each J-pole antenna is arranged in a plane or defines a plane. Since the radiation section is typically linear, the plane is defined at least by the feed section of the J-pole antenna. Typically, the two legs of the "U" lie in the plane or span the plane. In particular, the radiation section and the feed section of an antenna together define the plane. The plane typically runs through the center of the cross-section of the feed and/or radiation section. The antenna extends mainly in the plane. The extension of the antenna perpendicular to the plane is then only small, for example less than 10% of the maximum extension of the antenna in the plane. The extension of the antenna outside the plane may be limited to the diameter or thickness of the antenna body, for example the feed section and/or the radiation section.

Typically, the planes of the antennas are arranged at alternating angles in relation to the reference surface. Typically, the feed sections of the antennas are arranged at alternating angles in relation to the reference surface. In particular, the two antennas themselves are also arranged at a non-zero angle to each other.

The reference surface is a surface in space. The reference surface may be flat (planar) or curved. The reference surface may be a virtual surface. The reference surface is typically not a purely random, arbitrary surface, but has an actual correspondence on the antenna assembly and/or a component comprising the antenna assembly. For example, the reference surface may be a surface of a component comprising the antenna assembly or may be a cladding of the antenna assembly or run parallel to such a cladding.

In the case of a cylindrical antenna assembly, for example in the form of a circular cylinder, the reference surface can, for example, be the lateral surface of the cylinder. In the case of a flat antenna assembly, the reference surface is in particular a common plane that runs through the antennas.

The antennas are arranged adjacent to each other. If there are more than two antennas, no further antenna is therefore arranged between the two antennas. If there are more than two antennas, no further antenna is closer to one of the two antennas than the other of the two antennas. In the case of a plurality of antennas, the two antennas are, in other words, any first antenna of the plurality of antennas and a second antenna which, starting from the first antenna, is the antenna with the smallest distance or, if several different antennas have the same smallest distance from the first antenna, one of the plurality of antennas with the smallest distance. This applies in particular with regard to the reference surface. In other words, there is no other antenna on or at the reference surface that is closer to one of the two antennas. In particular, the antennas are accordingly arranged adjacent to each other with respect to the reference surface.

It is possible that the two antennas are spaced apart. It is not excluded that a cavity and/or one or more other elements are present between the antennas. It is therefore not necessary for the antennas to directly adjoin or border one another.

The at least two antennas are arranged alternately at a first angle and a second angle in relation to a reference surface. A first antenna is arranged at the first angle to the reference surface. A second antenna is arranged at a second angle to the reference surface. A third antenna, if present, is again arranged at the first angle to the reference surface, and so on. The first angle and the second angle are different.

If only two antennas are present, "alternating" means that the first antenna is arranged at the first angle to the reference surface and the second antenna is arranged at the second angle to the reference surface. In this case, the reference surface is typically flat. In particular, the antennas are aligned at an angle of 90° to each other.

Typically, the antenna assembly comprises at least three antennas. Each of the three antennas is designed as a J-pole antenna and two of the antennas-in this case, for example, three antennas—are arranged adjacent to each other, respectively. In other words, the first and second antennas are adjacent and the second and third antennas are adjacent. The antennas are arranged alternately at a first angle and a second angle in relation to the reference surface. The first and third antennas are therefore arranged at the same angle to the reference surface. The second antenna is arranged at a different angle to the reference surface. In the case of a fourth antenna, which is arranged adjacent to the third antenna, it would be arranged at the same angle to the reference surface as the second antenna. This results in the alternating arrangement.

The antenna is a transmitting and/or receiving device for an imaging method. It can be a pure transmitting antenna (transmit-only antenna). In MRI, for example, the antenna is used to generate or transmit high-frequency (RF) excitation pulses, in particular a high-frequency alternating magnetic field, and/or to receive or detect magnetic resonance signals, in particular by detecting an electrical voltage induced in the antenna. In particular, the antenna is a high-frequency antenna that operates at a frequency in the radio wave range or radio frequency range, in particular in the MHz range, and/or is designed for such a range. Future applications could also operate in the GHz range. It can therefore generate and/or detect a high-frequency field. It can also be referred to as a radio frequency or RF antenna.

The imaging method is typically a diagnostic and/or medical method. In particular, it is used to take images of a body or part of a body of a living being, for example a human being, from which information about a state of health of the living being can be derived.

In one embodiment, the first angle and the second angle have a difference of 90°. The position of the first antenna in relation to the reference surface differs from the position of the second antenna in relation to the reference surface by 90°. If the reference surface is flat, for example, the antennas are therefore arranged alternately offset by 90° to each other. If the first and third antennas are arranged at an angle of 0° to the reference surface, the second antenna is arranged at an angle of 90° to the reference surface, for example. If the first and third antennas are arranged at an angle of 30° to the reference surface, the second antenna is arranged at an angle of 120° to the reference surface, for example.

If the reference surface is, for example, a lateral surface of a circular cylinder, the first antenna is arranged at a first angle in relation to the lateral surface and the second antenna is arranged at a second angle in relation to the lateral surface, which is offset by 90° in relation to the first angle. If the first angle is 0°, then the second angle is 90°. The first antenna is thus arranged parallel to the lateral surface, i.e., tangentially, and the second antenna is arranged along the radius of the circle, i.e., radially. This creates an alternating arrangement around the circumference of the circle. In this case, the adjacent antennas do not have an angle of 90° to each other, but a smaller angle, which depends on the angle between the antennas measured from the central axis of the circular cylinder, i.e., for example on the number of antennas distributed around the circumference. This embodiment enables particularly extensive decoupling due to the maximum difference in the angles between the antennas.

In one embodiment, a first antenna of the two antennas is aligned essentially along the reference surface and a second antenna of the two antennas is aligned essentially perpendicular to the reference surface. Along the reference surface means in the reference surface or parallel to the reference surface. If the reference surface is curved, a tangential course is meant, for example. The antennas can, for example, be arranged alternately vertically and horizontally. This enables a particularly simple design that allows extensive decoupling.

In one embodiment, the at least two antennas are arranged in such a way that the two antennas form an angle $\gamma$ between each other. $\gamma$ is greater than 25° and/or less than or equal to 90°. In particular, $\gamma$ is $\geq$45°, preferably $\gamma\geq$60°. The feed sections of the two antennas and/or the planes of neighboring antennas form the angle $\gamma$ between each other. The angle $\gamma$ is the smaller angle measured between the planes of the two antennas. Accordingly, the angle $\gamma$ is less than or equal to 90°. In the case of a cylinder, the angle is measured in particular parallel to the longitudinal axis of the cylinder.

If the angle $\gamma$ is 90°, maximum decoupling is achieved. In this case, the resulting fields, or more precisely the B1 field directions of the antennas, are perpendicular to each other so that there is no or only minimal mutual interference or coupling. If the angle is 0, on the other hand, there is no decoupling. Therefore, angles $\gamma$ that approach 90° are generally desirable.

In one embodiment, the angle $\gamma$ is greater than 30°, in particular greater than 45°. In one configuration, the angle is $\gamma\geq$60°, in particular $\gamma\geq$70° and preferably $\gamma\geq$80°. For geometric reasons and/or depending on the specific application, angles of 90° or close to 90° cannot always be realized. Even at 30°, 45° or 60°, however, there is still sufficient decoupling. Depending on the application, smaller angles are therefore also possible, as these still result in an improved decoupling compared to conventional antenna assemblies.

For example, if the antenna assembly forms a circular cylindrical hollow body, the antennas are basically arranged in a regular n-gon. With six antennas, for example, this results in a hexagon, so that an angle of 60° already consists between two adjacent antennas in a conventional arrangement. Due to the alternating arrangement according to the present disclosure, the angle between the antennas is then only 30°.

In one configuration, in at least one antenna, the leg of the feed section adjoining the radiation section is arranged on the same straight line as the radiation section. In other words, the radiation section and the feed section merge in a straight line. In an alternative or supplementary configuration, in at least one antenna, the leg of the feed section adjoining the radiation section is arranged at an angle to the radiation section. In other words, there is a kink and/or a bend between the radiation section and the feed section. This can also be referred to as an antenna with an inclined feed section.

In one embodiment, the antenna assembly comprises at least three, in particular four or more antennas, which are designed as a J-pole antenna with a radiation section and a feed section. The antennas are arranged alternately at the first angle and the second angle in relation to the reference surface.

In one embodiment, the antenna assembly has 4 or more antennas, preferably 6 or more antennas, and/or 32 or fewer antennas, in particular 20 or fewer antennas, in one configuration 16 or fewer antennas. In antenna assemblies for examining the human head, for example, 6 to 8 antennas can be used. In antenna assemblies for examining the entire human body, for example, 16 to 32 antennas can be used. Such a large number is only possible using the decoupling assembly according to the present disclosure.

All antennas of the antenna assembly can be arranged alternately at the first and second angle in relation to the reference surface. In this case, there is no antenna that is not decoupled in accordance with the present disclosure. In this way, maximum decoupling is achieved overall.

In one embodiment, the antenna assembly is an antenna assembly for magnetic resonance imaging (MRI), ultra-high field MRI, MR positron emission tomography (MR-PET), MR single proton emission computed tomography (MR-SPECT), MR-Linac (linear accelerator combined with a magnetic resonance tomograph) and/or MR-guided ultrasound. In one configuration, the antenna assembly is an antenna assembly for MRI or ultra-high field MRI. This means that the antennas of the antenna assembly are suitable for performing MRI or ultra-high field MRI and/or for use in an MRI system. In one configuration, the antenna assembly is an antenna assembly for MR-PET and/or MR-SPECT. In one configuration, the antenna assembly is an antenna assembly for a combination of two or more of said methods.

PET and SPECT are methods in which radioactive tracers are used to visualize certain metabolic processes and/or molecular pathways. In this way, insights into physiological and metabolic processes can be obtained with a high degree of specificity and sensitivity. According to the present disclosure, the antenna assembly can be used for a combination of these methods with MR.

In particular for MRI applications, the antenna assembly may comprise at least one pair of antennas arranged according to the present disclosure and additionally one or more single antennas, for example J-pole antennas. In areas where a high density of antennas is required, this can thus be specifically achieved by decoupling according to the present disclosure. Alternatively or additionally, the antenna assembly can have a conventional antenna.

In one embodiment, the antenna assembly is an antenna assembly for simultaneous MR-PET/-SPECT. Simultaneous MR-PET/SPECT allows to simultaneously perform magnetic resonance imaging and PET/SPECT. Since the J-pole antenna can function as an MRI antenna and can be configured such that it does not have any highly attenuating materials, such as high-density materials, a particularly low attenuation of only around 15% is achieved for PET/SPECT. At the same time, a high signal-to-noise ratio in the order of conventional dipole antennas can be achieved with MRI. The decoupling now achieved can further increase B1 homogeneity and image quality.

Previous decoupling methods cannot be used with PET/SPECT as they comprise the use of highly attenuating and scattering materials, such as capacitors or coaxial cables, at unevenly distributed points in the PET/SPECT field of view (FOV). This causes severe artifacts and reduces the sensitivity of the PET/SPECT. In contrast, the decoupling according to the present disclosure by means of the alternating angular arrangement of the antennas is suitable for PET/SPECT due to the absence of strongly attenuating and/or scattering materials in the FOV.

In one embodiment, the radiation section of each of the two antennas is produced from a material essentially transparent to PET and/or SPECT, for example copper or aluminum. Materials essentially transparent to PET and/or SPECT bring low to negligible attenuation and scattering in PET and/or SPECT. In particular, the material essentially transparent to PET and/or SPECT is a metal with a low atomic number. Copper and aluminum are particularly suitable materials for the radiation section. In this way, the antenna assembly can be used as described in tomography systems for simultaneous MR-PET/SPECT. In one configuration, the radiation section of each of the two antennas is very thin. Very thin means in particular that the radiation section is at most a factor of 3 to 5 thicker than the skin depth at the desired frequency.

In one embodiment, the antennas of the antenna assembly define a hollow body in which a body or a body part can be arranged. The antennas are arranged around the hollow body. In particular, the radiation parts of the antennas are arranged around the hollow body and/or define the hollow body. In this way, a human or animal body or a part thereof can be accommodated in the hollow body and irradiated there.

In one embodiment, the hollow body has a circular cylindrical basic shape. In this case, the antennas can, for example, be arranged in a regular polygon, such as a regular hexagon, octagon or dodecagon, when viewed along the central axis of the basic shape.

In one embodiment, the antenna assembly has a radiation part and a feed part adjacent to the radiation part. The radiation sections of the antennas are arranged in the radiation part. The feed sections of the antennas are arranged in the feed part. In other words, the entire antenna assembly is divided into two separate parts, a radiation part and a feed part. The feed part typically comprises all feed sections, so that there are no feed sections in the radiation part. All feed sections are then arranged in the feed part. The radiation part can therefore be arranged in the measuring range of the tomography system.

In one embodiment, the antenna assembly has at least two antennas, which are designed as J-pole antennas with a radiation section and a feed section. The radiation sections of the two antennas are arranged crossing each other. This means that the radiation sections cross each other (form a cross) in at least one viewing direction. The radiation sections form an angle α to each other that is not equal to zero. The angle α may be between 30° and 90°, in particular between 45° and 90°. The antenna assembly may have several pairs of two intersecting antennas, respectively.

An effective electromagnetic decoupling of the two antennas from each other is also achieved by the mutually crossing arrangement of the radiation sections. Two different types of decoupling can therefore be combined with each other. For example, there may be pairs of antennas that are arranged crossing each other and other pairs of antennas that are arranged alternately at an angle in relation to a reference surface. Alternatively or additionally, at least one pair of antennas arranged crossing each other can be arranged alternately with a further antenna or a further pair of antennas arranged crossing each other at an angle in relation to a reference surface.

A further aspect of the present disclosure is the use of an antenna assembly in a tomography system, in particular for MRI or simultaneous MR-PET/SPECT. In particular, the antenna assembly is arranged such that the feed sections are located outside a measuring range of the tomography system. All features, embodiments and advantages of the antenna assembly described above also apply to the use and vice versa.

A further aspect of the present disclosure is a tomography system, in particular for MRI or simultaneous MR-PET/SPECT. The tomography system comprises an antenna assembly. In particular, the antenna assembly is arranged such that the feed sections are located outside a measuring range of the tomography system.

All features, embodiments and advantages of the antenna assembly described above and of its use also apply to the tomography system and vice versa.

Further exemplary embodiments of the invention are explained in more detail below, also with reference to figures.

BRIEF DESCRIPTIONS OF THE DRAWINGS

Figure 2:
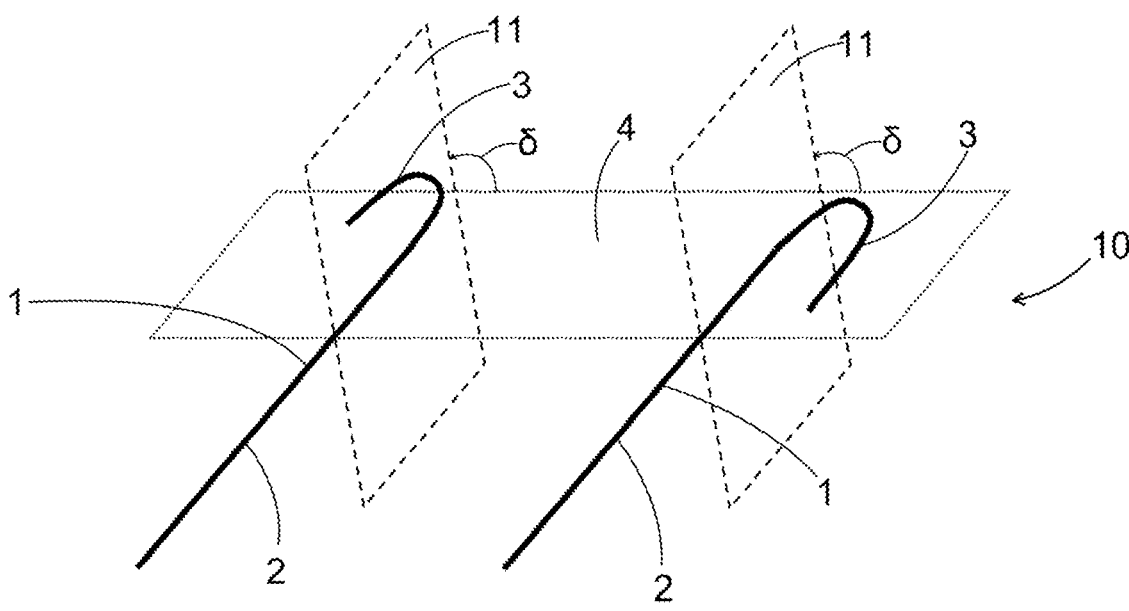
Figure 3:
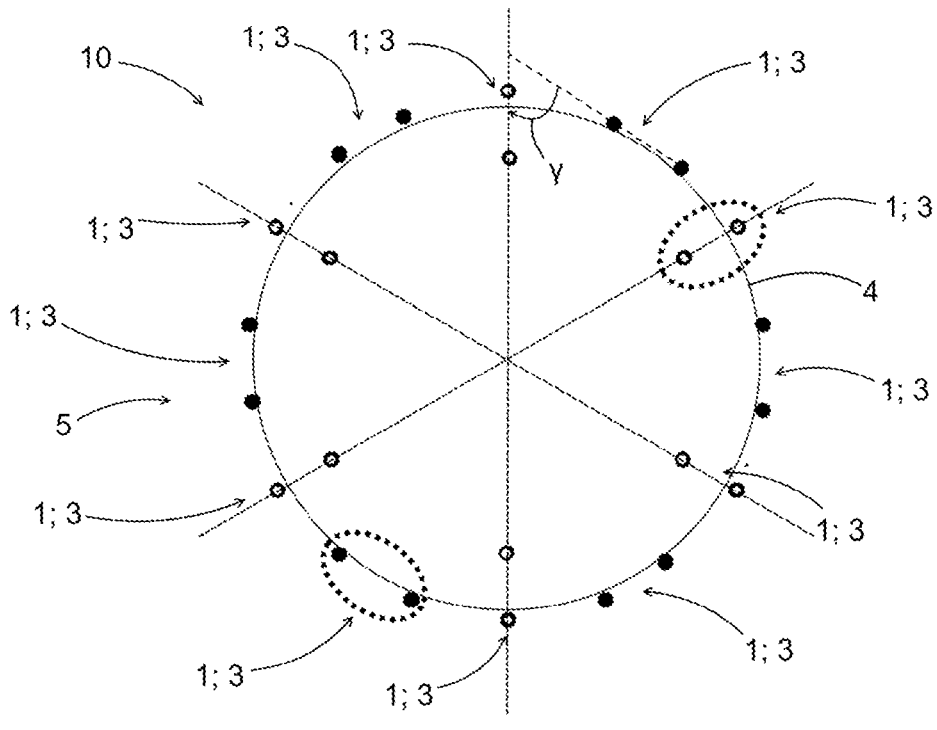
Figure 4:
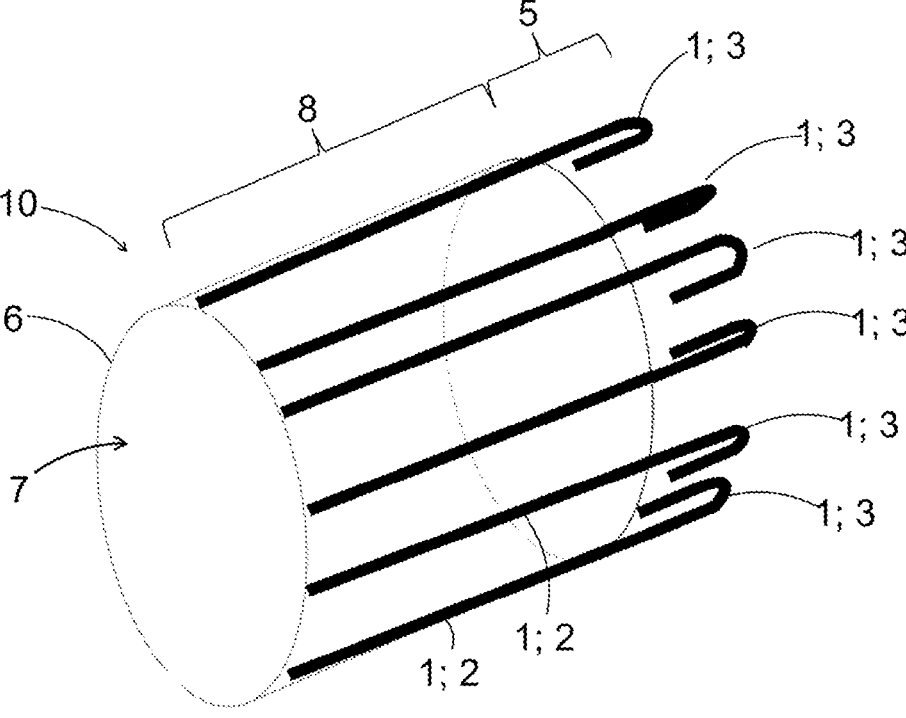

The figures show:

FIG. 1: a schematic representation of a J-pole antenna;

FIG. 2: a schematic perspective representation of an antenna assembly;

FIG. 3: a sectional drawing of a further embodiment of an antenna assembly;

FIG. 4: a perspective representation of an antenna assembly; and

Figure 5:
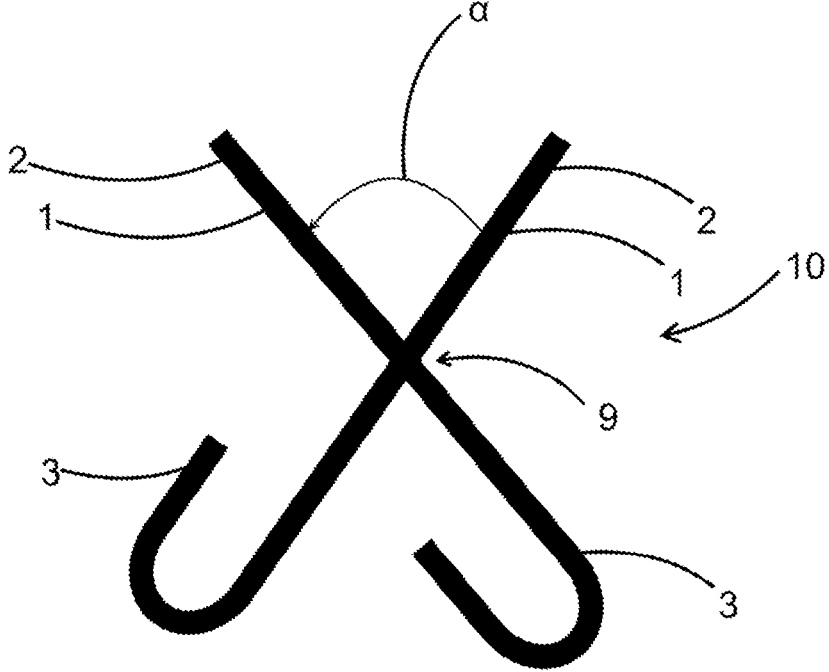

FIG. 5: a schematic representation of an antenna assembly with two antennas whose radiation sections are arranged crossing each other.

DETAILED DESCRIPTION

FIG. 1 shows an antenna 1 in the shape of a J-pole antenna. This comprises a straight radiation section 2 and an immediately adjacent feed section 3. The feed section 3 is U-shaped. The radiation section 2 merges seamlessly into a leg of the "U". This creates the characteristic J-shape of antenna 1.

The radiation section 2 serves for transmitting and receiving or exclusively transmitting electromagnetic signals of an imaging method such as, for example, MRI or simultaneous MR-PET/SPECT. The feed section 3 is used to feed the antenna 1, or more precisely the radiation section 2.

In particular, the cross-section of the antenna 1 does not cause any abrupt changes in the absorption coefficients for γ-radiation. For example, the cross-section is circular or elliptical. This can prevent artifacts in PET/SPECT imaging. The antenna 1 is preferably thin. In the sense of the present disclosure, thin means, for example, a thickness corresponding to 3 to 5 times the penetration depth of the radio frequency field into the antenna.

The two dotted lines mark the upper end of the antenna 1 and the boundary between the radiation section 2 and the feed section 3. The length of the radiation section 2 between the two dotted lines is typically λ/2. The length of the feed section 3 from the lower dotted line to the lower end of the U-shape is typically λ/4. This can be adapted as described above.

FIG. 2 shows a first embodiment of an antenna assembly 10 according to the present disclosure. Two J-pole antennas 1 are arranged adjacent to each other in or on a flat reference surface 4. The first antenna 1 shown on the left is arranged in an auxiliary plane 11; both legs of the U-shaped feed section 3 are therefore located in the auxiliary plane 11. The radiation section 2 and the immediately adjacent lower leg of the "U" are arranged in the reference surface 4. In this example, the auxiliary plane 11 is aligned at an angle δ of 90° to the reference surface 4. The first antenna 1 shown on the left is therefore arranged at a first angle of 90° to the reference surface.

The second antenna 1 shown on the right is rotated clockwise by 90° compared to this. Both legs of the U-shaped feed section 3 of this second antenna 1 lie in or on the reference surface. The second antenna 1 is thus arranged at a second angle of 0° to the reference surface. In this way, the alternating arrangement according to the present disclosure is produced. Thus, a decoupling of the two antennas 1 from each other is achieved, which enables an arrangement of more antennas 1 per volume or per surface. In this way, the imaging method is improved, in particular the uniformity and the signal-to-noise ratio are increased. In the event that a third antenna 1 were present to the right of the second antenna 1, it would be arranged at a first angle of 90° to the reference surface in the same way as the first antenna 1 according to the present disclosure in order to achieve the alternating arrangement.

FIG. 3 shows a sectional drawing through an antenna assembly 10 with a circular cylindrical basic shape in the radial direction. There are twelve antennas 1 evenly distributed around the circumference of the circle. The sectional plane shown runs through the feed part 5 of the antenna assembly 10 (cf. FIG. 4), so that each antenna 1 is represented by two conductors with a circular cross-section, which represent the legs of the "U". The plane of each antenna 1 is spanned by these two conductors.

The reference surface 4 is the lateral surface of the circle. It is therefore a curved reference surface 4. The antennas 1 are arranged alternately at an angle of 0° and 90° to the reference surface 4. The antennas 1 are therefore alternately aligned along the reference surface 4 (shown as filled circles) and perpendicular to the reference surface 4 (shown as circles with a white core). For clarity, one antenna 1 of each of the two described orientations is circled with a dotted line and thus highlighted. Neighboring antennas 1 have an angle γ between them, which is 60° here due to the twelve antennas. If fewer antennas are distributed around the circumference, the angle γ is also smaller. Despite the angle γ deviating from 90°, good decoupling of the antennas is achieved. The antennas 1 aligned perpendicular to the reference surface 4 are arranged here, for example, so that the outer conductor lies approximately on the arc of the circle. Deviating from this, individual or all of the antennas 1 aligned perpendicular to the reference surface 4 can also be shifted further outwards or bent so that, for example, the respectively inner conductor lies approximately on the arc of the circle.

FIG. 4 shows an antenna assembly 10, e.g., the antenna assembly 10 of FIG. 3, in perspective view. It can be seen that the antenna assembly 10 defines a hollow body 6. The individual antennas 1 surround this hollow body 6, which has a circular cylindrical basic shape 7. A body part or a body can be accommodated in the hollow body 6 in order to be examined using the imaging method. The radiation sections 2 of the antennas 1 together form a radiation part 8 of the antenna assembly 10. The feed sections of the antennas 1 together form a feed part 5 of the antenna assembly 10, which directly adjoins the radiation part. Thus, the radiation sections 2 of the antennas 1 all have the same orientation, namely parallel to the longitudinal extension of the cylinder. For reasons of clarity, only six antennas 1 are shown. However, a total of twelve antennas 1 are typically present here. It can be seen that the feed sections 3, as already shown in FIG. 3, are alternately aligned tangentially and radially.

FIG. 5 shows an antenna assembly 10 with two antennas 1 whose radiation sections 2 are arranged crossing each other. The antennas are configured as J-pole antennas. A crossing point 9 is formed. The two antennas 1 form an angle α of approximately 75° between each other. The angle α is the smaller angle measured between the radiation sections 2 of the two antennas 1. In this way, decoupling of the two antennas 1 from each other is achieved, which allows more antennas 1 to be arranged per volume or per area. In this way, the imaging method is improved, in particular the resolution is increased. This embodiment can be combined as desired with the alternating angular arrangement of the antennas 1 described above in order to achieve a further improved decoupling.

In particular, the antenna assembly 10 comprises a positioning unit for positioning the antennas 1 in relation to each other and/or to a body to be examined. This can be designed as a holding device for holding the antennas 1 and/or as a fastening unit for mechanically fastening the antennas 1 to one another. The positioning unit can, for example, have the basic circular cylindrical shape 7. The positioning unit may be adapted to the shape and/or size of the body or body part to be examined, here for example the human head.

LIST OF REFERENCE SIGNS

Antenna 1
Radiation section 2
Feed section 3
Reference surface 4
Feed part 5
Hollow body 6
Circular cylindrical basic shape 7
Radiation part 8
Crossing point 9
Antenna assembly 10
Auxiliary plane 11
Angle α
Angle δ
Angle γ

The invention claimed is:

1. An antenna assembly for an imaging method, the antenna assembly comprising
   at least two adjacent antennas, wherein each of the at least two antennas is configured as a J-pole antenna with a radiation section and a feed section,
   wherein the at least two antennas are arranged alternately at a first angle and a second angle different from the first angle in relation to a reference surface, and
   wherein the antenna assembly comprises at least three antennas which are designed as J-pole antennas and are arranged alternately at the first angle and the second angle in relation to the reference surface.

2. The antenna assembly of claim 1, wherein the first angle and the second angle have a difference of 90°.

3. The antenna assembly of claim 2, wherein a first antenna of the two antennas is aligned substantially along the reference surface and a second antenna of the two antennas is aligned substantially perpendicular to the reference surface.

4. The antenna assembly of claim 3, wherein the at least two antennas are arranged in such a way that the two antennas form an angle γ between each other, wherein γ is between 25° and 90°.

5. The antenna assembly of claim 1, wherein a first antenna of the two antennas is aligned substantially along the reference surface and a second antenna of the two antennas is aligned substantially perpendicular to the reference surface.

6. The antenna assembly of claim 1, wherein the at least two antennas are arranged in such a way that the two antennas form an angle γ between each other, wherein γ is between 25° and 90°.

7. The antenna assembly of claim 6, wherein γ≥45°.

8. The antenna assembly of claim 6, wherein γ≥60°.

9. The antenna assembly of claim 1, wherein the antenna assembly has between 4 and 32 antennas.

10. The antenna assembly of claim 9, wherein the antenna assembly has between 6 and 16 antennas.

11. The antenna assembly of claim 1, wherein the antenna assembly is an antenna assembly for magnetic resonance imaging (MRI), ultra-high field MRI, MR positron emission tomography (MR-PET), MR single proton emission computed tomography (MR-SPECT), MR linear accelerator and/or MR ultrasound.

12. The antenna assembly of claim 1, wherein the antenna assembly is an antenna assembly for simultaneous MR-PET/-SPECT.

13. The antenna assembly of claim 1, wherein the radiation section of each of the two antennas is produced from a material substantially transparent to PET and/or SPECT.

14. The antenna assembly of claim 1, wherein the antennas of the antenna assembly define a hollow body in which a body or a body part can be arranged.

15. The antenna assembly of claim 14, wherein the hollow body has a circular cylindrical basic shape.

16. The antenna assembly of claim 1, wherein the antenna assembly has a radiation part and a feed part adjacent to the radiation part, wherein the radiation sections of the antennas are arranged in the radiation part and the feed sections of the antennas are arranged in the feed part.

17. The antenna assembly of claim 1, wherein the antenna assembly has at least two antennas which are designed as J-pole antennas with a radiation section and a feed section, wherein the radiation sections of the two antennas are arranged crossing each other.

18. A method of using an antenna assembly in a tomography system, the method comprising providing the antenna assembly having at least two adjacent antennas, wherein each of the at least two antennas is configured as a J-pole antenna with a radiation section and a feed section, and wherein the at least two antennas are arranged alternately at a first angle and a second angle different from the first angle in relation to a reference surface, and acquiring imaging via MRI or simultaneous MR-PET/-SPECT using the antenna assembly.

19. A tomography system, adapted for MRI or simultaneous MR-PET/SPECT, the system comprising an antenna assembly having at least two adjacent antennas, wherein each of the at least two antennas is configured as a J-pole antenna with a radiation section and a feed section, and wherein the at least two antennas are arranged alternately at a first angle and a second angle different from the first angle in relation to a reference surface, and wherein the antenna assembly is arranged in particular such that the feed sections are located outside a measuring range of the tomography system.

* * * * *